United States Patent
Matsumoto (10) Patent No.: US 10,538,729 B2
(45) Date of Patent: Jan. 21, 2020

(54) CELL IMAGING CONTROL DEVICE, METHOD, AND PROGRAM

(71) Applicant: FUJIFILM Corporation, Tokyo (JP)

(72) Inventor: Tsuyoshi Matsumoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 743 days.

(21) Appl. No.: 15/251,193

(22) Filed: Aug. 30, 2016

(65) Prior Publication Data
US 2016/0369223 A1 Dec. 22, 2016

Related U.S. Application Data

(63) Continuation of application No. PCT/JP2015/051072, filed on Jan. 16, 2015.

(30) Foreign Application Priority Data

Mar. 4, 2014 (JP) .................. 2014-041687

(51) Int. Cl.
*G01C 3/08* (2006.01)
*C12M 1/34* (2006.01)
(Continued)

(52) U.S. Cl.
CPC ............. *C12M 41/36* (2013.01); *G02B 21/14* (2013.01); *G02B 21/244* (2013.01); *G02B 21/365* (2013.01)

(58) Field of Classification Search
CPC .... G02B 21/004; G02B 21/14; G02B 21/086; G02B 21/365; G06K 9/00127;
(Continued)

(56) References Cited

U.S. PATENT DOCUMENTS

| 2001/0033414 A1 | 10/2001 | Yahiro |
| 2012/0120302 A1 | 5/2012 | Kiyota et al. |
| 2013/0188033 A1* | 7/2013 | Oda .................. G01N 15/1463 348/79 |

FOREIGN PATENT DOCUMENTS

| JP | 2001-296478 A | 10/2001 |
| JP | 2006-3543 A | 1/2006 |

(Continued)

OTHER PUBLICATIONS

International Search Report, issued in PCT/JP2015/051072, dated Apr. 14, 2015.
(Continued)

*Primary Examiner* — Mark Hellner
(74) *Attorney, Agent, or Firm* — Birch, Stewart, Kolasch & Birch, LLP (57) ABSTRACT

There is provided a cell imaging control device, method, and a non-transitory computer readable recording medium recorded with a program capable of performing focus control more efficiently when imaging cells being cultured and improving the focus accuracy. There are included: an information acquisition unit 22 that acquires at least one of information regarding the maturity of cells being cultured or observation position information of the cells in a colony; a focus parameter determination unit 23 that determines a focus parameter based on at least one of the information regarding the maturity of the cells or the observation position information; and a focus control section 25 that performs focus control in an imaging device, which captures an image of the cells, based on the focus parameter.

20 Claims, 6 Drawing Sheets

(51) Int. Cl.
*G02B 21/24* (2006.01)
*G02B 21/14* (2006.01)
*G02B 21/36* (2006.01)

(58) Field of Classification Search
CPC ... G06K 9/4604; G06K 9/0014; C12M 41/46; C12M 41/36; C12M 41/48; G01N 15/1475; G01N 15/1463; G01N 2015/0065; G01N 2015/1006
USPC .......................................................... 356/4.04
See application file for complete search history.

(56) References Cited

FOREIGN PATENT DOCUMENTS

| | | |
|---|---|---|
| JP | 2009-198525 A | 9/2009 |
| JP | 2011-22322 A | 2/2011 |
| JP | 2013-44967 A | 3/2013 |
| WO | WO 2009/125547 A1 | 10/2009 |
| WO | WO 2010/128670 A1 | 11/2010 |

OTHER PUBLICATIONS

Written Opinion of the International Searching Authority, issued in PCT/JP2015/051072 (PCT/ISA/237), dated Apr. 14, 2015.
English Translation of International Preliminary Report on Patentability (including PCT/IB/373 and PCT/ISA/237) for PCT/JP2015/051072, dated Sep. 6, 2016.

* cited by examiner

| TYPE OF CELL | CULTURE CONDITIONS | | CULTURE PERIOD | FOCUS SEARCH INITIAL POSITION IN CENTRAL PORTION (OFFSET AMOUNT FROM BOTTOM) | FOCUS SEARCH INITIAL POSITION IN PERIPHERAL PORTION (OFFSET AMOUNT FROM BOTTOM) |
|---|---|---|---|---|---|
| iPS | CONDITIONS A | | EARLY STAGE | SMALL | SMALL |
| | | | MIDDLE STAGE | LARGE | SMALL |
| | | | LATE STAGE | SMALL | SMALL |
| | CONDITIONS B | | EARLY STAGE | SMALL | SMALL |
| | | | MIDDLE STAGE | LARGE | SMALL |
| | | | LATE STAGE | LARGE | LARGE |
| ES | CONDITIONS A | | EARLY STAGE | ... | ... |
| | | | MIDDLE STAGE | | |
| | | | LATE STAGE | | |
| | CONDITIONS C | | EARLY STAGE | | |
| | | | MIDDLE STAGE | | |
| | | | LATE STAGE | | |

FIG. 6

CELL IMAGING CONTROL DEVICE, METHOD, AND PROGRAM

CROSS-REFERENCE TO RELATED APPLICATIONS

This application is a Continuation of PCT International Application No. PCT/JP2015/051072 filed on Jan. 16, 2015, which claims priority under 35 U.S.C § 119(a) to Japanese Patent Application No. 2014-041687 filed on Mar. 4, 2014. Each of the above application(s) is hereby expressly incorporated by reference, in its entirety, into the present application.

BACKGROUND OF THE INVENTION

1. Field of the Invention

The present invention relates to a cell imaging control device, method, and a non-transitory computer readable recording medium recorded with a program for performing focus control of an imaging device for imaging cells.

2. Description of the Related Art

Conventionally, a method of temporally imaging pluripotent stem cells, such as ES cells, iPS cells, and STAP cells, or differentiation-induced cells and performing quality determination of the culture state of the cells by checking a temporal variation in the image has been proposed.

In addition, as a device for imaging cells as described above, a microscope is used. However, when capturing an image of cells with a microscope, so-called autofocus control is performed so that the image of cells is captured in a state of an optimal focus position.

As a device for imaging cells by such autofocus control, JP2011-022322A has proposed acquiring a focus position by performing autofocus control for each cell and storing the focus position and information of a vessel, in which cells are cultured, so as to match each other.

JP2013-044967A has proposed a method of acquiring a focus position by performing autofocus control based on a bright-field image and acquiring a focus position at the time of fluorescence observation by adding an offset according to the type of target molecule to the acquired focus position.

JP2001-296478A, JP2009-198525A, and JP2006-003543A have proposed offsetting a focus according to a type of each of cells, the shape of a well bottom, and the thickness of a culture medium.

WO2010/128670A has proposed performing autofocus control based on unevenness information of lighting. WO2009/125547A has proposed performing autofocus control by limiting the focus search range when acquiring the position of an embryo, which is a subject, and imaging the embryo at high magnification based on the position.

SUMMARY OF THE INVENTION

Here, for example, when culturing stem cells as described above, the form of a stem cell colony changes according to the culture period. Specifically, as culturing of a stem cell colony progresses, undifferentiated cells become more densely located in the central portion of the stem cell colony, and changes from the undifferentiated cells to differentiated cells occur in the peripheral portion. Since the ratio of nucleus/cytoplasm is different between undifferentiated cells and differentiated cells, the height of the cell nucleus from the cell mounting surface is different between the central portion and the peripheral portion of the stem cell colony.

If autofocus control is performed in such a state so that all cell nuclei in the stem cell colony are searched for, the measurement time taken to find the optimal focus position is increased since the search range is wide. In addition, the amount of data of a cell image for each focus position acquired at that time is also increased.

In JP2011-022322A, JP2013-044967A, JP2001-296478A, JP2009-198525A, JP2006-003543A, WO2010/128670A, and WO2009/125547A, there are no proposals for a method of solving the problem described above. In addition, in the related art, focus parameters are just determined based on predetermined conditions, information, and the like at an initial time. Accordingly, since the form of each cell changes with the growth of the cell (passage of time) as described above, there is a problem that the accuracy of autofocusing is lowered.

In view of the aforementioned problems, it is an object of the present invention to provide a cell imaging control device, method, and a non-transitory computer readable recording medium recorded with a program capable of performing focus control more efficiently when imaging cells being cultured and improving the focus accuracy.

A cell imaging control device of the present invention comprises: an information acquisition unit that acquires at least one of information regarding maturity of cells being cultured or observation position information of the cells in a colony; a focus parameter determination unit that determines a focus parameter based on at least one of the information regarding the maturity of the cells or the observation position information acquired by the information acquisition unit; and a focus control unit that performs focus control in an imaging device, which captures an image of the cells, based on the focus parameter.

The cell imaging control device of the present invention may further comprise an image acquisition unit that acquires an image of the cells, and the information acquisition unit may acquire the information regarding the maturity by analyzing the image of the cells.

An image acquisition unit that acquires an image of the cells and a colony region specifying unit that specifies a region of a colony of the cells in the image of the cells may be provided, and the information acquisition unit may acquire the observation position information by receiving a designation of a position in the colony region specified by the colony region specifying unit.

An image acquisition unit that acquires an image of the cells and a colony region specifying unit that specifies a region of a colony of the cells in the image of the cells may be provided, and the information acquisition unit may acquire the observation position information based on image information in the colony region specified by the colony region specifying unit.

As the information regarding the maturity, a culture period of the cells can be acquired.

As the focus parameter, at least one of a focus search initial position, a focus search range, a focus search width, a focus search order, or the number of focus operations can be determined.

The focus parameter determination unit may have a function showing a relationship between the observation position information and a focus search initial position, and the focus search initial position may be determined as the focus parameter based on the function and the observation position information.

The function may be a function in which the focus search initial position changes in a Gaussian distribution shape as a position indicated by the observation position information moves to a peripheral portion from a central portion of the colony of the cells.

The information acquisition unit may acquire both the information regarding the maturity and the observation position information. In a case where a focus search initial position is determined as the focus parameter and the observation position information is a peripheral portion in a colony of the cells, the focus parameter determination unit may determine the focus search initial position as being closer to a mounting surface side of the cells as the maturity increases.

The information acquisition unit may acquire both the information regarding the maturity and the observation position information. In a case where a focus search initial position is determined as the focus parameter and the observation position information is a central portion in a colony of the cells, the focus parameter determination unit may determine the focus search initial position as being further from a mounting surface of the cells in a case where the maturity is a middle stage than in a case where the maturity is an early stage and a late stage.

A cell imaging control method of the present invention using the cell imaging control device includes: acquiring at least one of information regarding maturity of cells being cultured or observation position information of the cells in a colony; determining a focus parameter based on at least one of the information regarding the maturity of the cells or the observation position information; and performing focus control in an imaging device, which captures an image of the cells, based on the determined focus parameter.

A non-transitory computer readable recording medium recorded with a cell imaging control program of the present invention causes a computer to function as the cell imaging control device comprising: an information acquisition unit that acquires at least one of information regarding maturity of cells being cultured or observation position information of the cells in a colony; a focus parameter determination unit that determines a focus parameter based on at least one of the information regarding the maturity of the cells or the observation position information acquired by the information acquisition unit; and a focus control unit that performs focus control in an imaging device, which captures an image of the cells, based on the focus parameter determined by the focus parameter determination unit.

According to the cell imaging control device, method, and a non-transitory computer readable recording medium recorded with a program of the present invention, at least one of the information regarding the maturity of cells being cultured or the observation position information of the cells in a colony is acquired, a focus parameter is determined based on at least one of the information regarding the maturity of the cells or the observation position information, and focus control in the imaging device that captures an image of the cells may be performed based on the determined focus parameter. Accordingly, for example, if the focus search initial position is determined according to the maturity of cells or the observation position in the cell colony, it is possible to search for the focus position more efficiently, and the data amount of a cell image captured for each focus position can also be reduced. In addition, it is possible to improve the focus accuracy.

DESCRIPTION OF THE PREFERRED EMBODIMENTS

Figure 1:
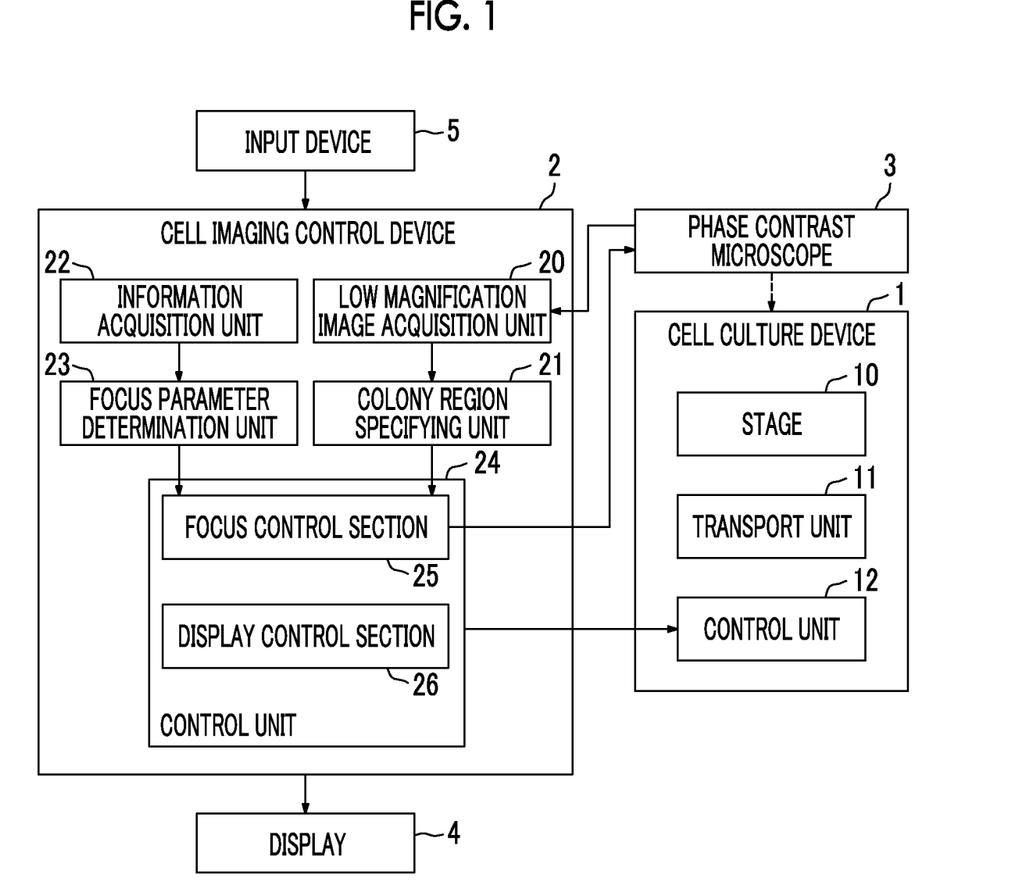
FIG. 1 is a block diagram showing the schematic configuration of a stem cell culture observation system using an embodiment of a cell imaging control device of the present invention.

Hereinafter, a cell culture observation system using an embodiment of a cell imaging control device, method, and a non-transitory computer readable recording medium recorded with a program of the present invention will be described in detail with reference to the diagrams. First, the overall structure will be described. FIG. 1 is a block diagram showing the schematic configuration of a stem cell culture observation system.

As shown in FIG. 1, the stem cell culture observation system of the present embodiment includes a cell culture device 1, a cell imaging control device 2, a phase contrast microscope 3, a display 4, and an input device 5.

The cell culture device 1 is a device for culturing cells. As cells to be cultured, for example, there are stem cells such as iPS cells, ES cells, and STAP cells, cells of nerves, skin, and liver that are differentiation-induced from stem cells, and cancer cells. In the cell culture device 1, a plurality of culture vessels are housed in which stem cells to be cultured are seeded on a culture medium. The cell culture device 1 includes a stage 10, a transport unit 11, and a control unit 12.

On the stage 10, a culture vessel to be imaged by the phase contrast microscope 3 is placed. As the culture vessel, there is a plate on which stem cells are plane-cultured or a flask in which stem cells are suspension-cultured. The stage 10 is configured to be movable in X and Y directions perpendicular to each other within the mounting surface of the culture vessel by a driving mechanism (not shown). In addition, a direction perpendicular to the X and Y directions is a Z direction. A focus position is changed in the Z direction, thereby performing focus control. The focus control will be described in detail later.

The transport unit 11 selects a culture vessel to be imaged from a plurality of culture vessels housed in a predetermined position in the cell culture device 1, and transports the selected culture vessel to the stage 10.

The control unit 12 controls the entire cell culture device 1, and controls not only the operation of the stage 10 or the transport unit 11 but also environmental conditions, such as the temperature, humidity, and $CO_2$ concentration in the cell culture device 1. As the configuration for adjusting the temperature, humidity, and $CO_2$ concentration, it is possible to use a known configuration.

The phase contrast microscope 3 corresponds to an imaging device, and captures phase images of cells within the culture vessel placed on the stage 10. The phase contrast microscope 3 of the present embodiment has an autofocus function of changing the focus position automatically, and performs focus control based on the focus control signal output from a focus control section 25 to be described later.

Figure 2:
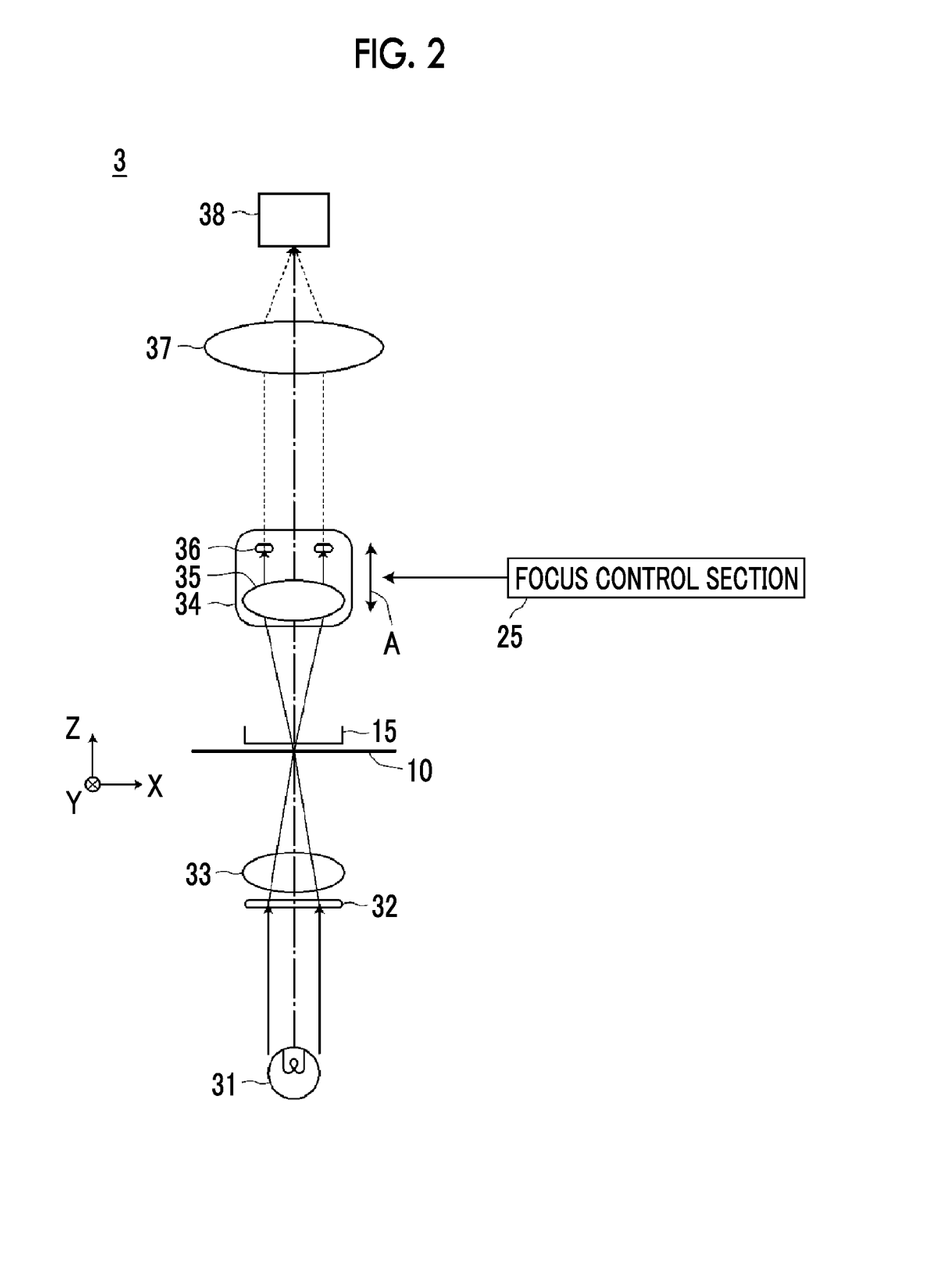
FIG. 2 is a diagram showing the schematic configuration of a phase contrast microscope.

FIG. 2 is a diagram showing the schematic configuration of the phase contrast microscope 3. As shown in FIG. 2, the phase contrast microscope 3 includes: a white light source 31 which emits white light; a slit plate 32 which has a ring-shaped slit, on which the white light emitted from the white light source 31 is incident, and which emits ring-shaped illumination light; and an objective lens 33 on which the ring-shaped illumination light emitted from the slit plate 32 is incident and which emits the incident ring-shaped illumination light to cells in a culture vessel 15 placed on the stage 10.

In addition, a phase difference lens 34, an imaging lens 37, and an imaging element 38 are provided on the opposite side to the white light source 31 with respect to the stage 10.

The phase difference lens 34 includes an objective lens 35 and a phase plate 36. The phase plate 36 is configured by forming a phase ring on a transparent plate that is transparent for the wavelength of the ring-shaped illumination light. In addition, the size of the slit of the slit plate 32 described above and the phase ring is in the conjugate relationship.

The phase ring is configured by forming a phase film, which shifts the phase of incident light by ¼ wavelength, and a dimming filter for dimming the incident light in a ring shape. Direct light incident on the phase difference lens 34 is condensed by the objective lens 35, and is transmitted through the phase ring. As a result, the phase of the direct light is shifted by ¼ wavelength, and the brightness is weakened. On the other hand, most of the diffracted light diffracted by the cells in the culture vessel 15 passes through the transparent plate of the phase plate, and the phase and the brightness are not changed.

The phase difference lens 34 is moved in the arrow A direction shown in FIG. 2 by a driving mechanism (not shown). A focus position is changed by such movement of the phase difference lens 34, so that the focus control is performed. The driving mechanism moves the phase difference lens 34 based on the focus control signal output from the focus control section 25 of the cell imaging control device 2.

In addition, the phase contrast microscope 3 of the present embodiment is configured such that a plurality of phase difference lenses 34 having different magnifications are replaceable. For the replacement of the phase difference lens 34, automatic replacement may be performed according to an instruction input from the user, or manual replacement may be performed by the user.

In the present embodiment, low magnification imaging for macro observation and high magnification imaging for detailed observation are performed. The 1× to 4× phase difference lens 34 is used at the time of low magnification imaging, and 10× to 20× phase difference lens 34 is used at the time of high magnification imaging. However, the low magnification imaging and the high magnification imaging may be performed with relatively different magnifications, and are not limited to such magnification.

Direct light and diffracted light that are transmitted through the phase difference lens 34 are incident on the imaging lens 37, and an image of these light beams is formed on the imaging element 38. The imaging element 38 captures a phase image of cells by performing photoelectric conversion of the image formed by the imaging lens 37. As the imaging element 38, a charge-coupled device (CCD) image sensor, a complementary metal-oxide semiconductor (CMOS) image sensor, or the like can be used.

Although the phase contrast microscope 3 is used as an imaging device in the present embodiment, microscopes having other autofocus functions may be used. For example, a differential interference microscope may be used.

Referring back to FIG. 1, the cell imaging control device 2 includes a low magnification image acquisition unit 20, a colony region specifying unit 21, an information acquisition unit 22, a focus parameter determination unit 23, and a control unit 24. The control unit 24 includes the focus control section 25 and a display control section 26.

The cell imaging control device 2 is formed by installing an embodiment of a cell imaging control program of the present invention in a computer. The cell imaging control device 2 includes a central processing unit, a semiconductor memory, a hard disk, and the like, and an embodiment of the cell imaging control program is installed in the hard disk. When the program is executed by the control unit 24 having a central processing unit, the low magnification image acquisition unit 20, the colony region specifying unit 21, the information acquisition unit 22, the focus parameter determination unit 23, the focus control section 25, and the display control section 26 shown in FIG. 1 operate.

The low magnification image acquisition unit 20 acquires a cell image obtained by performing the above-described low magnification imaging by the phase contrast microscope 3. As the low magnification cell image acquired by the low magnification image acquisition unit 20, one image may be acquired by imaging one cell colony, or a group of a plurality of images may be acquired by dividing one cell colony into a plurality of rectangular divided regions. In addition, a plurality of cell colonies may be included in one image.

The low magnification image acquisition unit 20 stores identification information for identifying a cell colony and a low magnification cell image so as to match each other. For example, in a case where one cell colony is captured as one low magnification cell image, identification information of the cell colony and the low magnification cell image are stored so as to match each other in a one-to-one manner. In a case where one cell colony is captured as low magnification cell images of a plurality of divided regions, identification information of the cell colony and the low magnification cell images of the plurality of divided regions are stored so as to match each other. In addition, in a case where a plurality of cell colonies are captured as one low magnification cell image, identification information of each of the cell colonies and one low magnification cell image are stored so as to match each other.

By managing the identification information of each cell colony and a low magnification cell image so as to match each other as described above, for example, when a user inputs the identification information of the cell colony through the input device 5, it is possible to immediately read and display the low magnification cell image matched with the identification information.

The colony region specifying unit 21 specifies a position of a cell colony region in the low magnification cell image acquired by the low magnification image acquisition unit 20. As a method of specifying a cell colony region, for example, it is desirable to specify the position of a cell colony region by converting a low magnification cell image into a binary image and then automatically extracting a cell colony region by template matching or the like. For the automatic extraction of a cell colony region, other known methods may be used without being limited to the method described above.

In addition, without being limited to the automatic extraction, a low magnification cell image may be displayed on the display 4 by the display control section 26, the user may designate a cell colony region in the low magnification cell image using the input device 5, and the colony region specifying unit 21 may acquire position information, such as the designated coordinates.

The information acquisition unit 22 acquires cell type information, information of culture conditions, information regarding the maturity of cells, and observation position information in a cell colony. The above information acquired by the information acquisition unit 22 is used when determining focus parameters that are used for autofocus control in the focus parameter determination unit 23.

As the cell type information, for example, there are iPS cells, ES cells, and myocardial cells or liver cells after induction of differentiation. Since the size (height in the Z direction) changes with a type of each of cells, it is possible to set the upper limit or lower limit of the focus search range of the autofocus by acquiring the cell type information. The cell type information is not limited to the cells listed above, and other pieces of type information may be included.

In the present embodiment, the maturity of cells is divided into three stages of an early stage of culture, a middle stage of culture, a late stage of culture, and information regarding the maturity of cells is acquired by the information acquisition unit 22, thereby acquiring a stage to which the maturity of cells to be imaged belongs.

The reason why the maturity of cells is divided into the early stage of culture, the middle stage of culture, the late stage of culture is that the form of a cell colony differs depending on each of the stages and it is desirable to set the focus search initial position of the autofocus according to the form.

Figure 3:
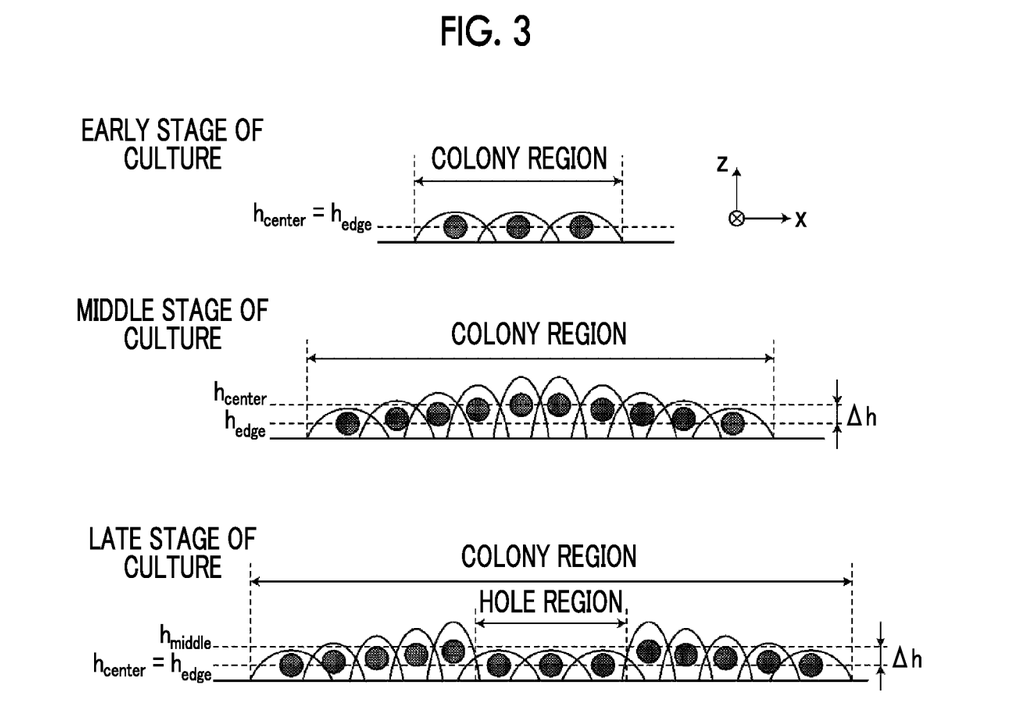
FIG. 3 is a diagram showing an example of the form of a stem cell colony in the early stage of culture, the middle stage of culture, and the late stage of culture.

Specifically, for example, in the case of a stem cell colony, in the early stage of culture, undifferentiated cells are uniformly distributed in a colony region example as shown in FIG. 3. Accordingly, the height $h_{center}$ of the nucleus of a stem cell in a central portion of the colony region is the same as the height $h_{edge}$ of the nucleus of a stem cell in a peripheral portion of the colony region.

Figure 4:
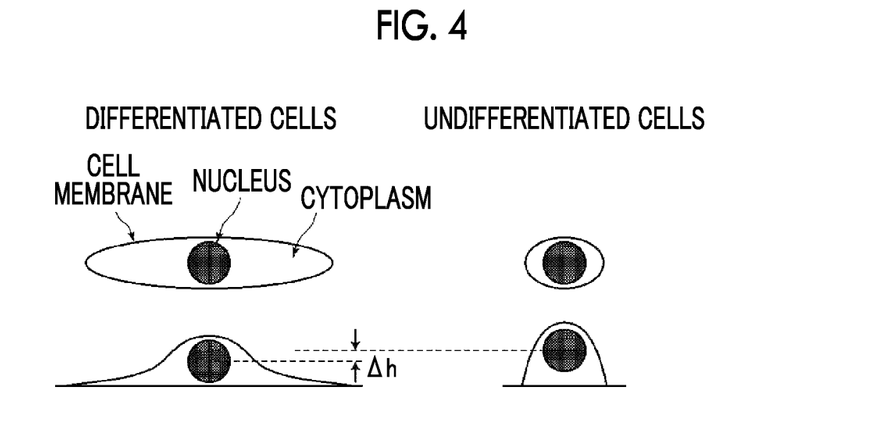
FIG. 4 is a diagram illustrating the ratio of nucleus/cytoplasm of undifferentiated cells and differentiated cells.

Then, in the middle stage of culture, as shown in FIG. 3, undifferentiated cells are densely distributed in the central portion of the colony region, and differentiation starts and differentiated cells are distributed in the peripheral portion of the colony region. FIG. 4 shows plan views (upper part of the figure) and elevation views (lower part of the figure) of undifferentiated cells and differentiated cells. Since the ratio of nucleus/cytoplasm in the differentiated cell is smaller than that in the undifferentiated cell, the height of the nucleus is low. Accordingly, as shown in FIG. 3, the height $h_{center}$ of the nucleus of the stem cell in the central portion of the colony region is larger than the height $h_{edge}$ of the nucleus of the stem cell in the peripheral portion of the colony region by $\Delta h$.

Then, in the late stage of culture, as shown in FIG. 3, a phenomenon called a hole occurs in which differentiation occurs easily in the central portion of the colony region. Accordingly, the height $h_{center}$ of the nucleus of the stem cell in the central portion of the colony region is the same as the height $h_{edge}$ of the nucleus of the stem cell in the peripheral portion of the colony region. However, the height $h_{middle}$ of the nucleus of a stem cell in an intermediate portion between the central portion and the peripheral portion is higher than the height $h_{center}$ and the height $h_{edge}$ by $\Delta h$.

As described above, the form of the cell colony region changes in the early stage of culture, the middle stage of culture, and the late stage of culture. Therefore, in the present embodiment, the focus search initial position of the autofocus is set according to the form change.

The information regarding the maturity of cells that is acquired by the information acquisition unit 22 may be any information indicating the stage of maturity of cells. For example, a culture period measured by a timer or the like can be acquired as the information regarding the maturity. Without being limited to the culture period, for example, image information of the cell colony region in a low magnification cell image may be analyzed, the size of the cell colony, the number of cells in the stem cell colony, or the number of cells per unit area smaller than the stem cell colony may be measured, and such information may be acquired as the information regarding the maturity. For example, it is determined that the maturity increases as the measured number of cells increases. The image information of the cell colony region may be acquired based on the position information of the cell colony specified by the colony region specifying unit 21.

As the size of the cell colony, it is possible to acquire the area, perimeter, maximum diameter, and the like of the cell colony. For the measurement of the number of cells in the cell colony, for example, it is preferable to detect each cell or the nucleus or nucleolus in the cell by pattern matching or the like and to count the number of detected cells.

In addition, for example, the brightness of the image of a cell colony region or a texture, such as uniformity or asperity, may be acquired as the information regarding the maturity. For example, in a case where cells to be imaged are stem cells, as the maturity increases, the density of stem cells increases, stem cells are further laminated, and the brightness of an image is gradually increased. Accordingly, it can be said that the maturity increases as the brightness increases.

In addition, in a case where the maturity increases and stem cells proliferate to be laminated as described above, the uniformity of the image becomes high, and a smooth image with a small amount of irregularities is obtained. Accordingly, it can be said that the maturity increases as the uniformity of an image becomes high and as the image becomes smooth. As a method of acquiring the feature quantity amount of the uniformity or smoothness of the image, it is possible to use a known method.

In addition, as the information regarding the maturity, the feature quantity of the shape of each stem cell colony may be acquired. As the maturity of the stem cell increases, the shape of the stem cell colony gradually approaches a circle. Then, differentiation in a peripheral portion progresses, and the complexity of the edge is increased. Therefore, such a feature quantity of change in the shape of the stein cell colony can be acquired as the feature quantity related to the maturity.

In addition, as the information regarding the maturity, the feature quantity of the thickness of each stem cell colony may be acquired. As the maturity of the stem cell increases, the stem cell colony becomes thick gradually. Therefore, such a feature quantity of the thickness of the stem cell colony can be acquired as the feature quantity related to the maturity. The thickness of the stem cell colony may be measured by a measuring device that is separately provided.

In addition, a user may set and input the information regarding the maturity described above using the input device 5, and the user may input not only the culture period or the size of a cell colony described above but also the passage number of cells as the information regarding the maturity.

In the present embodiment, the maturity of cells is divided into three stages. However, the maturity of cells may be divided into two stages or four stages or more without being limited to the three stages. As an interval of each stage, various intervals can be set according to the culture conditions or the like.

In addition, as the culture conditions acquired by the information acquisition unit 22, there are conditions regarding the type of the scaffolding or the medium, conditions regarding whether to use heterologous cells (feeder cells) that are different types from cells to be cultured, and the like. Even if the culture period is the same, the stage of the maturity differs depending on the culture conditions. Therefore, in the present embodiment, the culture conditions are also taken into consideration to set the focus search initial position of the autofocus.

The culture conditions are not limited to the conditions described above, and may be any conditions as long as the conditions influence the growth rate of cells. For example, the environmental conditions of culture, such as temperature, humidity, or $CO_2$ concentration, may be included. The information of the culture conditions is set and input by the user using the input device 5, for example. However, for the temperature and the humidity described above, conditions measured by using a thermometer or a hygrometer may be used.

In addition, the observation position information in a cell colony acquired by the information acquisition unit 22 is coordinate information indicating a position where high magnification imaging is to be performed, which is a position in the X-Y direction in the cell colony region captured by low magnification imaging.

As described above, for example, in the cell colony region in the middle stage of culture and the late stage of culture shown in FIG. 3, the height of the nucleus changes with a position in the X-Y direction in the cell colony region. In the present embodiment, therefore, observation position information in a cell colony region is acquired, and the focus search initial position of the autofocus is set using the observation position information. For example, the observation position information in the cell colony region may be set and input by the user using the input device 5.

Without being limited thereto, a table in which the stage of maturity of cells is associated with observation position information may be stored, and the observation position information may be determined according to the stage of maturity of cells. For example, in a case where the stage of maturity of cells is the early stage of culture and the middle stage of culture, the center position of the cell colony may be acquired as the observation position information. In a case where the stage of maturity of cells is the late stage of culture, an intermediate portion between the central portion and the peripheral portion of the cell colony may be acquired as the observation position information so that undifferentiated cells are mainly observed. Without being limited thereto, in a case where the stage of maturity of cells is the early stage of culture, the center position of the cell colony may be acquired as the observation position information so that undifferentiated cells are mainly observed. In a case where the stage of maturity of cells is the middle stage of culture and the late stage of culture, the peripheral portion of the cell colony may be acquired as the observation position information so that differentiated cells are mainly observed.

Alternatively, the observation position information may be acquired by analyzing the image information of a cell colony region in a low magnification cell image. Specifically, the number of cells per unit area in a cell colony region may be measured as a density, and a position of the density equal to or greater than a threshold value set in advance or a position of the density less than the threshold value may be acquired as the observation position information. Alternatively, a position of the density equal to or greater than a threshold value set in advance may be acquired as the observation position information in a case where the stage of maturity of cells is the early stage of culture and the middle stage of culture, and a position of the density less than the threshold value set in advance may be acquired as the observation position information in a case where the stage of maturity of cells is the late stage of culture. That is, a determination method for setting the observation position information may be changed according to the stage of maturity of cells.

Then, the focus parameter determination unit 23 determines the focus parameters, which are used in the autofocus control of the phase contrast microscope 3, based on the cell type information, the information of the culture conditions, the information regarding the maturity of cells, and the observation position information in a cell colony, which have been acquired by the information acquisition unit 22.

Figure 5:
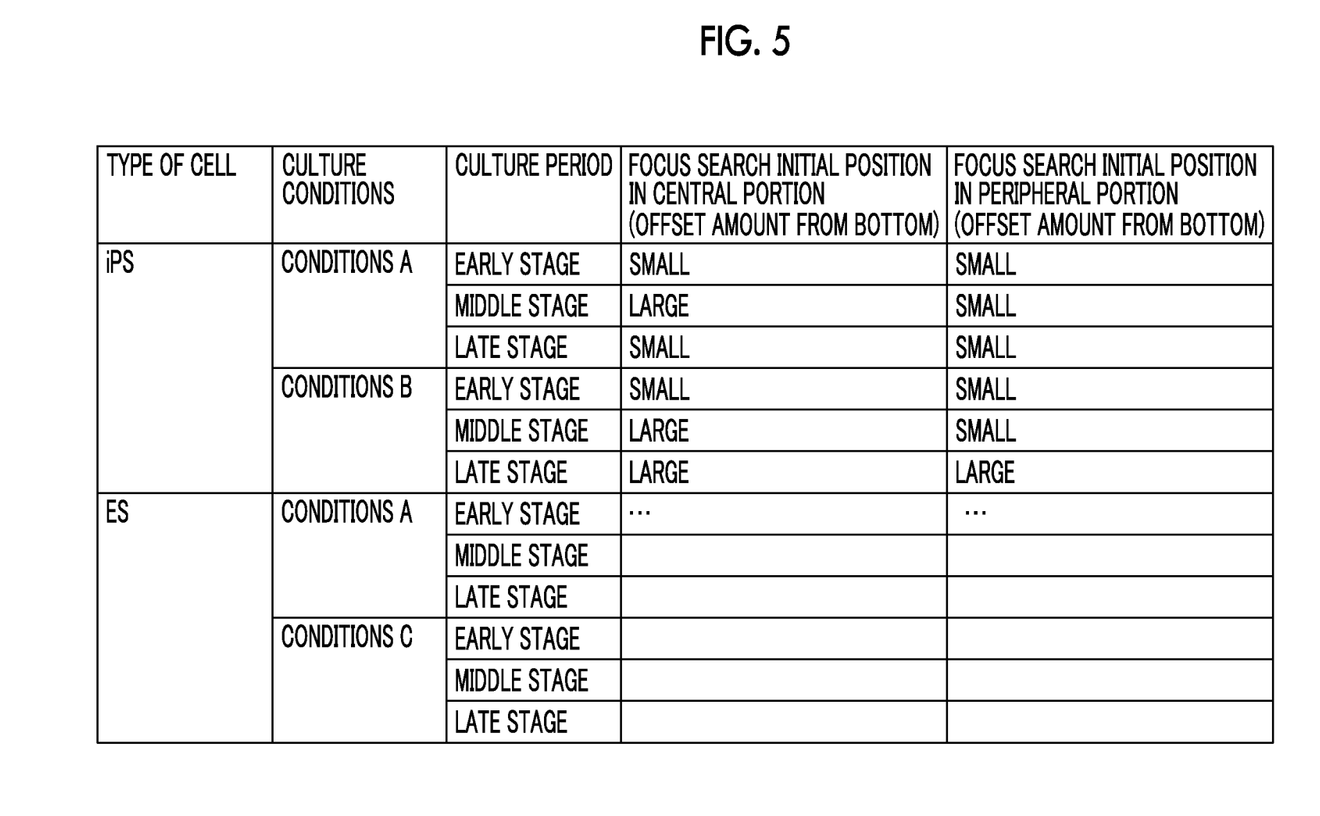
FIG. 5 is a diagram showing an example of a table in which a type of each of cells, culture conditions, a culture period, an observation position, and the focus search initial position of autofocusing are associated with each other.

FIG. 5 is a diagram showing an example of a table in which a type of each of cells, culture conditions, a culture period, an observation position, and the focus search initial position of the autofocus are associated with each other.

In the focus parameter determination unit 23, for example, the table shown in FIG. 5 is set in advance. Based on the information acquired by the information acquisition unit 22, the focus parameter determination unit 23 determines the focus search initial position by referring to the table shown in FIG. 5. In the table shown in FIG. 5, the relative relationship of the offset amount (distance) from the bottom of the culture vessel 15 is shown as the focus search initial position. In practice, however, the absolute value of the offset amount is acquired, and the offset amount is determined as the focus search initial position. In the table shown in FIG. 5, the offset amount of ES cells is not shown although the offset amount of ES cells is actually set.

Specifically, for example, in a case where the cell type information is an iPS cell, the information of culture conditions is conditions A, and the observation position information is a central portion, the offset amount of the focus search initial position may be relatively reduced (brought closer to the cell mounting surface side) in a case where the culture period is the early stage of culture and the late stage of culture, and the offset amount of the focus search initial position may be relatively increased (away from the cell mounting surface) in a case where the culture period is the middle stage of culture.

Similarly, even if the cell type information is an iPS cell and the information of culture conditions is conditions A, in a case where the observation position information is a peripheral portion, it is preferable to determine a relatively small offset amount without changing the offset amount according to the culture period.

Thus, by acquiring the offset amount with reference to the table shown in FIG. 5, it is possible to determine an appropriate focus search initial position according to the form of the cell colony.

For example, the focus search initial position corresponding to the observation position information in the cell colony region may be determined as discrete values based on the relative positional relationship from the reference position, such as a center position in the cell colony region, or may be determined as continuous values based on the relative positional relationship.

Specifically, for example, a distance from the reference position to the observation position may be set as a variable and a distance function for outputting a focus search initial position corresponding to the variable may be set in advance, and the focus search initial position may be determined based on the observation position and the distance function.

Figure 6:
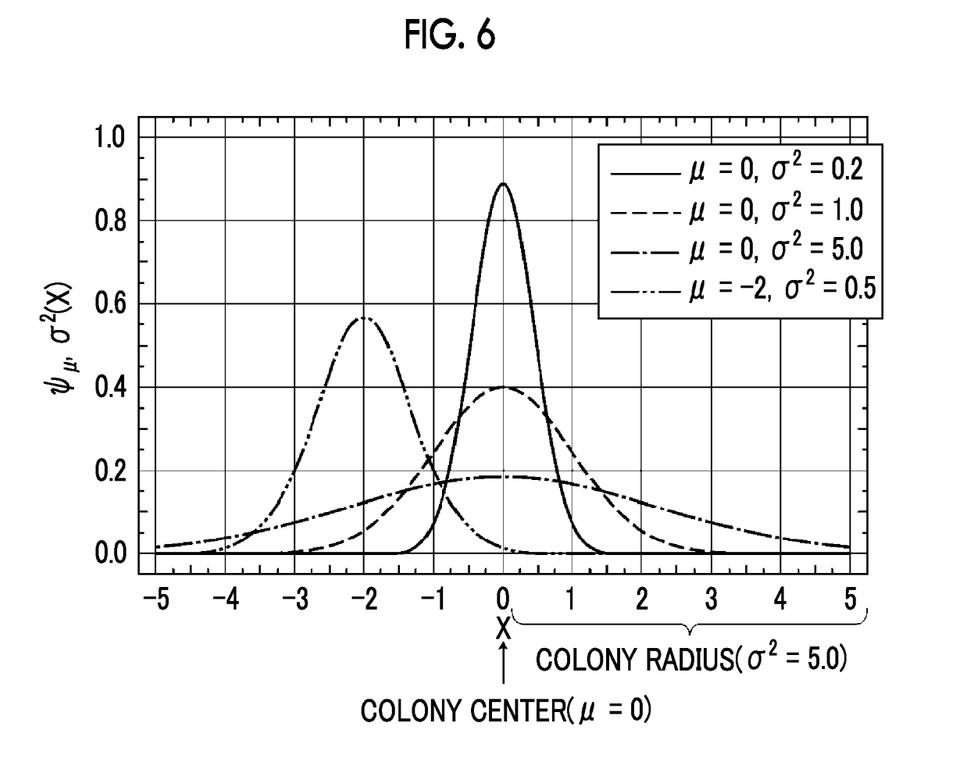
FIG. 6 is a diagram illustrating a distance function showing the relationship between the observation position information in a cell colony and focus parameters.

As a distance function, for example, in a case where a cell colony region is predicted to be circular, as shown in FIG. 6, it is possible to use a function of normal distribution, such as the following equation in which the center (reference position) of the cell colony region is an average μ of the normal distribution and the radius of the cell colony region is a dispersion σ² of the normal distribution. In FIG. 6, the lateral axis indicates a position in a cell colony region, and the vertical axis indicates a focus search initial position. In addition, a range from the zero of the vertical axis to the value of the graph can be used as a focus search range.

$$f(x) = \frac{1}{\sqrt{2\pi\sigma^2}} \exp\left(-\frac{(x-\mu)^2}{2\sigma^2}\right)$$ [Equation 1]

In the case of using such a function of normal distribution, the peak position of the normal distribution may be set to be in the center of the cell colony region (case of μ=0). In a case where it is predicted that a portion where cells are densely located is in a position shifted from the center of the cell colony region, the peak position may be offset (case of μ=−2 or the like). The cell colony region may have a shape other than a circle, and there are various ways in which cells are densely located. According to this, distance functions other than the normal distribution may be used. In addition, a distance function that changes discretely, such as a stepped pyramid shape, may be used.

The distance function described above may be set for each combination of cell type information, information of the culture conditions, and information of the culture period. Specifically, for example, it is preferable to set a distance function that reduces the offset amount of the peripheral portion of the cell colony region (brings the focus search initial position closer to the cell mounting surface side) as the culture period increases. At this time, for example, a distance function for each culture period may be set using a distance function in which the distance from the reference position to the observation position and the offset amount are associated with each other and a curve in which the culture period and the cell size are associated with each other, or a distance function for each culture period (density) may be set using a curve in which the density of cells and the height of the nucleus are associated with each other.

As shown in FIG. 3, in the late stage of culture, there is a case in which a hole is formed in the central portion of the cell colony region. In this case, therefore, a distance function of normal distribution may be set such that the intermediate portion between the central portion and the peripheral portion of the cell colony region becomes a peak position. In addition, since a hole spreads concentrically as the culture period increases, the peak position of the normal distribution may be moved toward the peripheral portion according to the culture period.

Alternatively, an absolute position and the focus search initial position may be associated with each other instead of determining the focus search initial position based on the relative positional relationship from the reference position as described above. The absolute position referred to herein is a relative position from the origin position when the entire culture region (for example, the entire well plate) in the culture vessel to be observed is viewed.

In addition, a thickness for each position within the X-Y plane of the bottom of the culture vessel 15, thickness information for each position within the X-Y plane of the scaffold, and the like may be further acquired, and the focus search initial position may be determined by also taking these into consideration.

Although the method of determining the focus search initial position in the autofocus has been described above, the focus parameter determination unit 23 also determines a focus search range, a focus search width, a focus search order, the number of focus operations, and the like.

The focus search range is a change range of the focus position in the autofocus control, and has a lower limit and an upper limit. For the focus search range, for example, a table in which a type of each of cells and the focus search range are associated with each other may be set in advance as described above, and the focus search range may be determined by referring to the above table based on the cell type information acquired by the information acquisition unit 22.

In addition, by setting a table, in which observation position information in a cell colony region and a focus search range are associated with each other, in advance or by using the distance function described above, a focus search range corresponding to the observation position information may be determined.

In addition, a table in which the culture period and the focus search range are associated with each other may be set in advance. In this case, for example, it is preferable to extend the focus search range as the culture period increases.

In addition, the focus search range may be determined for each combination of a type of each of cells, observation position information, and the culture period.

The focus search width is a change width at the time of one focus position change in the autofocus control. As the culture progresses to expand the cell colony, a variation in the density of cells may occur according to the location. Accordingly, in the focus search width that is set according to the early stage of culture in which a variation in the density of cells is small, a probability that the cell nucleus is out of the focus search range may be increased.

Therefore, for example, a table in which the culture period and the focus search width are associated with each other may be set in advance, and the focus search width may be made to extend as the culture period increases.

In addition, external force that each cell receives from surrounding cells is decreased toward the periphery of the cell colony region. Accordingly, each cell is easy to move, and the variation increases more. Therefore, a table in which the observation position information in a cell colony region and the focus search width are associated with each other may be set in advance, and the focus search width of the peripheral portion of the cell colony region may be larger than that of the central portion of the cell colony region.

In addition, the focus search width may be determined for each combination of the observation position information in a cell colony and the culture period.

As the focus search order, there are a case of performing autofocus control by sequentially changing the focus position from a high position to a low position with the bottom of the culture vessel 15 as a reference, a case of performing autofocus control by sequentially changing the focus position from the low position to the high position, and a case of performing autofocus control by alternately repeating a change in the focus position in a direction moving closer to the bottom of the culture vessel 15 and a change in the focus position in a direction away from the bottom of the culture vessel 15.

Since differentiated cells or cells around the colony are distributed to crawl on the bottom of the culture vessel 15 in many cases, it is efficient to search for the focus position from bottom side (low position) of the culture vessel 15. On the other hand, since undifferentiated cells or cells near the cell colony center stand in many cases, it is efficient to search for the focus position from a position away from the bottom of the culture vessel 15.

Accordingly, a table in which the observation position information in a cell colony region and the focus search order may be set in advance, and the focus position may be searched for toward the high position from the low position for the central portion of the cell colony region and the focus position may be searched for toward the low position from the high position for the peripheral portion of the cell colony region.

In addition, as the culture progresses, a variation in the focus position increases as described above. For this reason, searching for the focus position from a position between the high position and the low position rather than searching for the focus position from one of the high position and the low position is believed to be efficient as a whole since the number of searches in the entire cell colony is reduced.

Accordingly, for example, a table in which the culture period and the focus search order are associated with each other may be set in advance, and the focus position may be searched for toward the high position from the low position as described above in the early stage of culture or the middle stage of culture, and the focus position may be searched for by alternately repeating a search of the focus position from the high position and a search of the focus position from the low position in the late stage of culture.

In addition, the focus search order may be determined for each combination of the observation position information in a cell colony and the culture period.

The number of focus operations is an upper limit of the number of changes in the focus position in the autofocus control. In the early stage of culture to the middle stage of culture, in order to strictly recognize and evaluate the form of the cell nucleus or the equivalent tissue (for example, nucleolus), it can be said that strict focus accuracy is required. On the other hand, as the culture progresses, there is a tendency that the cell nucleus or the equivalent tissue is difficult to be visible due to differentiation or lamination of cells. In this case, it is believed that the strict focus accuracy is not required.

Therefore, for example, a table in which the culture period and the number of focus operations are associated with each other may be set in advance, and the number of focus operations may be made to decrease as the culture progresses. In contrast, there is also a case where there is a need to evaluate the expressed properties (chromatin condensation in the nucleus) as the culture progresses. In such a case, the focus accuracy may be increased by increasing the number of focus operations as the culture progresses.

In addition, a table in which the observation position information in a cell colony region and the number of focus operations are associated with each other may be set in advance, and the focus accuracy of the central portion may be increased by increasing the number of focus operations toward the central portion rather than the peripheral portion of the cell colony region. In contrast, in a case where it is necessary to concentrate on the observation of the peripheral portion of the cell colony region, the focus accuracy of the peripheral portion may be increased by increasing the number of focus operations toward the peripheral portion rather than the central portion of the cell colony region.

In addition, the number of focus operations may be determined for each combination of the observation position information in a cell colony and the culture period.

In addition, information of the amount of culture medium may be acquired by the information acquisition unit 22, and the focus search range may be determined by also taking the information into consideration. When culturing cells, suspended matter, such as dust or dead cells, may be present on the surface of the culture medium. In such a case, if autofocus control is performed based on the contrast of an image, a focus position is set on the surface of the culture medium on which suspended matter is present. For this reason, an appropriate cell image may not be able to be captured. Therefore, information of the surface position of the culture medium may be acquired by acquiring the information of the amount of culture medium, and the surface position may be removed from the autofocus search range. In addition, the information of the amount of culture medium may be set and input by the user using the input device 5.

Then, the focus control section 25 performs autofocus control by outputting a focus control signal to the phase contrast microscope 3 based on the focus parameters determined in the focus parameter determination unit 23 and moving the phase difference lens 34 in the phase contrast microscope 3 in the Z direction in response to the focus control signal. For the autofocus control, a method that is already known can be used. For example, the contrast of a cell image captured for each focus position may be calculated, and a focus position where the contrast becomes the maximum may be set as a final focus position.

The focus control section 25 outputs a control signal to the control unit 12 of the cell culture device 1 based on the position of the cell colony region specified by the colony region specifying unit 21 and the observation position information acquired by the information acquisition unit 22, and controls the movement of the stage 10 in the X-Y direction so that the above observation position in the cell colony region is imaged at high magnification.

Then, high magnification imaging is performed in a state in which the position of the culture vessel 15 in the X-Y direction and the focus position of the phase contrast microscope 3 have been adjusted by the focus control section 25. Accordingly, a high magnification cell image is captured.

The display control section 26 displays a low magnification cell image or a high magnification cell image on the display 4.

The input device 5 includes a mouse, a keyboard, and the like, and receives a setting input from the user. Specifically, the input device 5 receives a setting input of the cell type information, the culture conditions, the information regarding the maturity of cells, and the observation position information in a cell colony region that have been described above.

Figure 7:
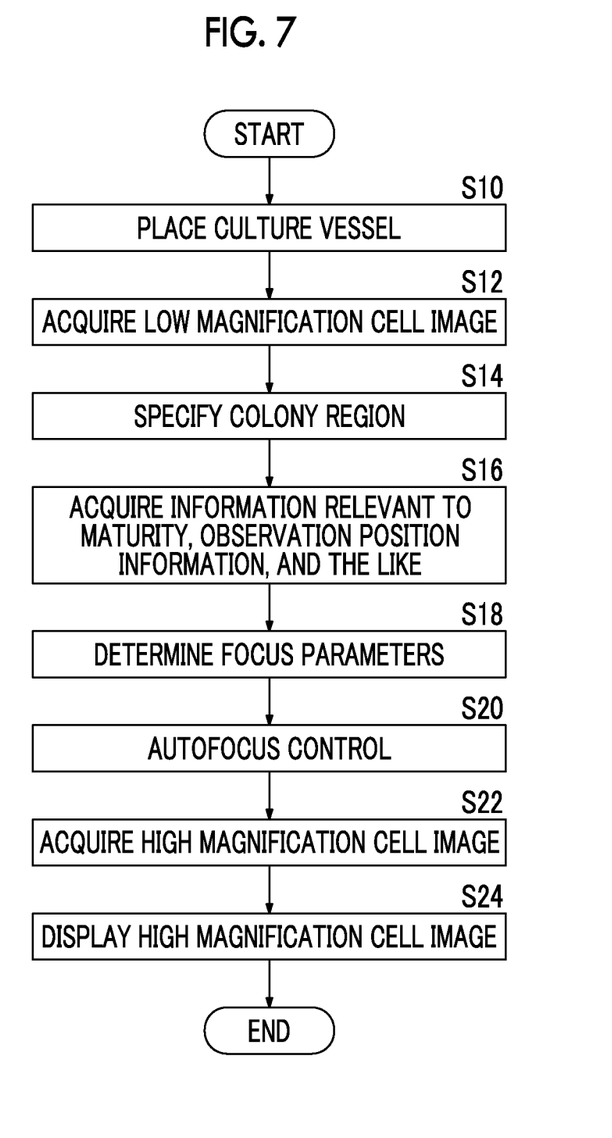
FIG. 7 is a flowchart illustrating the operation of the stem cell culture observation system using an embodiment of the cell imaging control device of the present invention.

Next, the operation of the above-described cell culture observation system will be described with reference to the flowchart shown in FIG. 7.

First, in the cell culture device 1, the transport unit 11 selects a culture vessel to be imaged from a plurality of culture vessels housed therein, and places the selected culture vessel 15 on the stage 10 (S10).

Then, the magnification of the phase difference lens 34 of the phase contrast microscope 3 is set to low magnification and a low magnification cell image is captured, and the low magnification cell image that has been captured is acquired by the low magnification image acquisition unit 20 (S12). The low magnification cell image acquired by the low magnification image acquisition unit 20 is output to the display control section 26, and is displayed on the display 4 by the display control section 26.

The low magnification cell image acquired by the low magnification image acquisition unit 20 is output to the colony region specifying unit 21, and the colony region specifying unit 21 specifies the position of a colony region in the low magnification cell image based on the input low magnification cell image (S14).

On the other hand, the information acquisition unit 22 acquires cell type information, information of culture conditions, information regarding the maturity of cells, and observation position information in a cell colony through a setting input or the like from the user (S16).

Then, the above information acquired by the information acquisition unit 22 is output to the focus parameter determination unit 23. The focus parameter determination unit 23 determines focus parameters, which are used in the autofocus control in the phase contrast microscope 3, based on the input information described above, and outputs the focus parameters to the focus control section 25 (S18).

The focus control section 25 moves the stage 10 in the X-Y direction so that the above observation position is captured at high magnification based on the position of the cell colony region specified by the colony region specifying unit 21 and the observation position information acquired by the information acquisition unit 22. Then, the focus control section 25 performs autofocus control of the phase contrast microscope 3 based on the input focus parameter (S20). At this time, the phase difference lens 34 in the phase contrast microscope 3 is replaced with the phase difference lens 34 for high magnification imaging.

Then, the phase contrast microscope 3 ends the autofocus, and captures a high magnification cell image for observation in a state in which the optimal focus position is set. The high magnification cell image captured by the phase contrast microscope 3 is acquired by the display control section 26 of the cell imaging control device 2 (S22), and the display control section 26 displays the input high magnification cell image for observation on the display 4 (S24).

According to the cell culture observation system of the embodiment described above, a culture period of cells being cultured and observation position information in a cell colony are acquired, focus parameters are determined based on the culture period and the observation position information that have been acquired, focus control in the imaging device that captures an image of cells is performed based on the determined focus parameters. Therefore, since it is possible to search for a focus position more efficiently, it is also possible to reduce the disease amount of the cell image captured for each focus position.

In the embodiment described above, the method of determining the focus parameters when imaging the stem cell colony has been described. However, an imaging target is not limited to the stem cell colony, and other types of cell colonies may be imaging targets. For example, the position information of blood vessels in a myocardial cell colony or a skin cell colony may be acquired as observation position information, and a focus search initial position corresponding to the observation position information may be determined. Also in this case, the focus search initial position may be changed according to the culture period. For example, the focus search initial position may be set to a deeper position (position closer to the cell mounting surface) as the culture period passes.

In addition, in the cell culture observation system of the embodiment described above, both the information regarding the maturity of cells, such as information of the culture period of cells, and the observation position information in a cell colony are acquired, and the focus parameters are determined based on these pieces of information. However, only one of these pieces of information may be acquired, and the focus parameters may be determined based on the information. For example, only the information of the culture period of cells may be acquired, and the focus search initial position may be determined according to the length of the culture period. In addition, only the observation position information in a cell colony may be acquired, and a focus search initial position where the offset amount of the peripheral portion in the cell colony region is smaller than that of the central portion in the cell colony region may be determined.

In addition, in the cell culture observation system of the embodiment described above, the focus search initial position, the focus search range, and the like are determined as focus parameters by the focus parameter determination unit 23, and autofocus control is performed by searching for the focus position based on these. However, without being limited thereto, for example, the focus parameter determination unit 23 may determine the focus position as a focus parameter, and the focus control section 25 may control the phase contrast microscope 3 to be placed at the focus position.

EXPLANATION OF REFERENCES

1: cell culture device
2: cell imaging control device
3: phase contrast microscope
4: display
5: input device
10: stage
11: transport unit
12: control unit
15: culture vessel
20: low magnification image acquisition unit
21: colony region specifying unit
22: information acquisition unit
23: focus parameter determination unit
24: control unit
25: focus control section
26: display control section
30: phase difference lens
31: white light source
32: slit plate
33: objective lens
34: phase difference lens
35: objective lens
36: phase plate
37: imaging lens
38: imaging element

What is claimed is:
1. A cell imaging control device, comprising:
a processor is configured to:
acquire at least one of information regarding maturity of cells being cultured or observation position information of the cells in a colony, determine a focus parameter based on at least one of the information regarding the maturity of the cells or the observation position information, and perform focus control in an imaging device, which captures an image of the cells, based on the focus parameter, wherein the focus parameter includes at least one of a focus search initial position, a focus search range, a focus search width, a focus search order, or the number of focus operations.

2. The cell imaging control device according to claim 1, wherein the processor is further configured to:

acquire an image of the cells, and acquire the information regarding the maturity by analyzing the image of the cells.

3. The cell imaging control device according to claim 1, wherein the processor is further configured to:

acquire an image of the cells, specify a region of a colony of the cells in the image of the cells, and acquire the observation position information by receiving a designation of a position in the colony region.

4. The cell imaging control device according to claim 1, wherein the processor is further configured to:

acquire an image of the cells, specify a region of a colony of the cells in the image of the cells, and acquire the observation position information based on image information in the colony region.

5. The cell imaging control device according to claim 1, wherein the information regarding the maturity is a culture period of the cells.

6. The cell imaging control device according to claim 2, wherein the information regarding the maturity is a culture period of the cells.

7. The cell imaging control device according to claim 3, wherein the information regarding the maturity is a culture period of the cells.

8. The cell imaging control device according to claim 4, wherein the information regarding the maturity is a culture period of the cells.

9. The cell imaging control device according to claim 2, wherein the focus parameter includes at least one of a focus search initial position, a focus search range, a focus search width, a focus search order, or the number of focus operations.

10. The cell imaging control device according to claim 3, wherein the focus parameter includes at least one of a focus search initial position, a focus search range, a focus search width, a focus search order, or the number of focus operations.

11. The cell imaging control device according to claim 4, wherein the focus parameter includes at least one of a focus search initial position, a focus search range, a focus search width, a focus search order, or the number of focus operations.

12. The cell imaging control device according to claim 5, wherein the focus parameter includes at least one of a focus search initial position, a focus search range, a focus search width, a focus search order, or the number of focus operations.

13. The cell imaging control device according to claim 1, wherein the processor is further configured to a function showing a relationship between the observation position information and a focus search initial position, and wherein the focus search initial position is determined as the focus parameter based on the function and the observation position information.

14. The cell imaging control device according to claim 2, wherein the processor is further configured to function showing a relationship between the observation position information and a focus search initial position, and wherein the focus search initial position is determined as the focus parameter based on the function and the observation position information.

15. The cell imaging control device according to claim 13, wherein the function is a function in which the focus search initial position changes in a Gaussian distribution shape as a position indicated by the observation position information moves to a peripheral portion from a central portion of the colony of the cells.

16. The cell imaging control device according to claim 1, wherein the processor is further configured to acquire both the information regarding the maturity and the observation position information, and in a case where a focus search initial position is determined as the focus parameter and the observation position information is a peripheral portion in a colony of the cells, the processor is further configured to determine the focus search initial position as being closer to a mounting surface side of the cells as the maturity increases.

17. The cell imaging control device according to claim 1, wherein the processor is further configured to acquire both the information regarding the maturity and the observation position information, and in a case where a focus search initial position is determined as the focus parameter and the observation position information is a central portion in a colony of the cells, the processor is further configured to determine the focus search initial position as being further from a mounting surface of the cells in a case where the maturity is a middle stage than in a case where the maturity is an early stage and a late stage.

18. A cell imaging control method using the cell imaging control device according to claim 1, comprising:

acquiring at least one of information regarding maturity of cells being cultured or observation position information of the cells in the colony;

determining the focus parameter based on at least one of the information regarding the maturity of the cells or the observation position information; and performing focus control in an imaging device, which captures the image of the cells, based on the determined focus parameter.

19. A non-transitory computer readable recording medium recorded with a cell imaging control program causing a computer to function as the cell imaging control device according to claim 1, the function comprising:

acquiring at least one of information regarding maturity of cells being cultured or observation position information of the cells in the colony;

determining the focus parameter based on at least one of the information regarding the maturity of the cells or the observation position information; and performing focus control in an imaging device, which captures the image of the cells, based on the focus parameter.

20. The cell imaging control device according to claim 1, wherein the processor is further configured to determine offset amount from a bottom of a culture vessel which contains the cells, as a focus search initial position.

* * * * *